(12) United States Patent
Song et al.

(10) Patent No.: US 7,070,950 B2
(45) Date of Patent: Jul. 4, 2006

(54) RECIPIENT BLOCK AND METHOD FOR PREPARATION THEREOF

(76) Inventors: Young-Min Song, #101-1501, Chunggu Apt., Mok-dong, Yangcheon-gu, Seoul, 158-050 (KR); Hyeong-Jae Jeong, #154-9, Garak-dong, Songpa-gu, Seoul, 138-809 (KR); Si-Chang Jang, #338-123, Hongeun 3-dong, Seodaemun-gu, Seoul, 120-848 (KR)

( * ) Notice: Subject to any disclaimer, the term of this patent is extended or adjusted under 35 U.S.C. 154(b) by 29 days.

(21) Appl. No.: 10/495,735

(22) PCT Filed: Apr. 6, 2004

(86) PCT No.: PCT/KR2004/000788

§ 371 (c)(1),
(2), (4) Date: May 14, 2004

(87) PCT Pub. No.: WO2004/111614

PCT Pub. Date: Dec. 23, 2004

(65) Prior Publication Data

US 2005/0176088 A1    Aug. 11, 2005

(30) Foreign Application Priority Data

Jun. 17, 2003    (KR) ...................... 20-2003-0019058

(51) Int. Cl.
*G01N 1/30*    (2006.01)
(52) U.S. Cl. .................... 435/40.5; 435/40.52
(58) Field of Classification Search ............ None
See application file for complete search history.

(56) References Cited

U.S. PATENT DOCUMENTS

| | | | |
|---|---|---|---|
| 4,820,504 A * | 4/1989 | Battifora | 435/7.23 |
| 6,207,408 B1 | 3/2001 | Essenfeld et al. | 435/40.5 |
| 6,451,551 B1 | 9/2002 | Zhan et al. | 435/40.52 |
| 2003/0040035 A1 | 2/2003 | Slamon | 435/40.5 |
| 2003/0119200 A1 | 6/2003 | Taft et al. | 436/176 |
| 2003/0138827 A1 | 7/2003 | Kononen et al. | 435/6 |

FOREIGN PATENT DOCUMENTS

| | | |
|---|---|---|
| KR | 20-0180302 | 5/2000 |
| WO | WO 01/51910 | 7/2001 |

OTHER PUBLICATIONS

Packeisen J et al, "Demystified . . . Tissue microarray technology"-review. J. Clin. Pathol: Mol. Pathol. 2003, 56: 198-204. Entire document.*
The term "additive" Merriam-Webster Online Dictionary. see at the web http:// www.m-w.com. p. 1.*
Moskaluk CA and Stoler MH. "Agarose mold embedding of cultured cells for tissue microarrays". Diagnostic Molecular Pathology, Dec. 2002 11(4): 234-238. entire document.*
Packeisen J et al. "Demystified . . . Tissue microarray technology". J. Clin. Pathol., 2003, 56: 198-204. entire document.*

* cited by examiner

*Primary Examiner*—Sandy E. Saucier
*Assistant Examiner*—Satyendra K. Singh
(74) *Attorney, Agent, or Firm*—Sheridan Ross P.C.

(57) ABSTRACT

Disclosed is a recipient block for arraying a certain tissue sample into a desired position on a tissue microarray slide, comprising (a) an additive and (b) a wax. The present invention also discloses a method of preparing a recipient block, including (1) preparing an aqueous solution of an additive; (2) pouring the aqueous solution of the additive into a mold and cooling the mold to gelate the aqueous solution of the additive; (3) dehydrating the resulting additive gel in alcohol; (4) immersing the dehydrated additive gel in an organic solvent to make the dehydrated additive gel transparent; (5) penetrating a wax into the transparent additive gel to provide a block; and (6) providing a plurality of cylindrical holes in the block. Further, the present invention discloses a method of preparing a tissue microarray block, including (1) arraying each of certain tissue samples into each of the cylindrical holes of the recipient block; and (2) heating the recipient block in which the tissue samples have been arrayed at 50° C. to 70° C. for 20 to 40 min and cooling the recipient block for embedding of the tissue samples.

19 Claims, 4 Drawing Sheets

Tissue microarray block

RECIPIENT BLOCK AND METHOD FOR PREPARATION THEREOF

This application is the U.S. National stage of International Application No. PCT/KR2004/000788, filed Apr. 6, 2004, which claims priority under 35 U.S.C. § 119 or 365 to Republic of Korean Application No. 20-2003-0019058, filed Jun. 17, 2003.

TECHNICAL FIELD

The present invention relates, in general, to a recipient block and a method of preparing thereof, and, more particularly, to a recipient block for arraying a certain tissue sample in a desired position on a slide, comprising (a) an additive and (b) a wax, a method of preparing the above recipient block, and a method of preparing a tissue microarray block using the recipient block.

BACKGROUND ART

A tissue microarray is an ordered array of numerous tissue samples, which is attached onto a single glass slide typically 2.5×7.5 cm in size, and also indicates a technology of preparing the above tissue array. Biological tissues useful in the tissue microarray include human tissues, animal tissues and cultured cells. A glass slide onto which a tissue microarray samples are attached is useful for analysis of intracellular proteins, DNA and RNA and microscopic analysis. The slide can be applied for a broad range of in situ assays, for examples, immunohistochemistry, in situ hybridization, special stain and in situ PCR.

In early days of medical and biological fields, biological tissue samples were analyzed at a state of being embedded in paraffin. The paraffin blocks were cut into thin sections (4–8 μm) using a tissue microtome and attached onto a glass slide. However, since the paraffin-embedded tissues in the blocks were bigger than 1×2×0.4 cm in size, only one tissue can be attached onto a single glass slide. Thus, especially when multiple tissue samples are desired to be analyzed, this conventional method is disadvantageous in terms of requiring many slides, many disposable materials and a large quantity of reagents, resulting in high costs for the analyses of the tissue samples, and time consuming. The disadvantages of the conventional method further may be lack of consistency and reliability since the tissue samples compared with each other, are analyzed separately by individual.

To overcome these problems, International Patent Application No. PCT/DE00/04647 discloses a method of preparing a recipient block capable of receiving multiple tissue samples. In detail, the method of preparing a recipient block comprises punching holes to the bottom of a tray-type aluminum block and striking a cylindrical pin into each hole. This provides a template for the recipient block; pouring a molten, high temperature paraffin solution into the template; and cooling the template to provide a plurality of cylindrical openings. The International Patent Application also discloses a method of preparing a tissue microarray block receiving multiple tissue samples, comprising arraying multiple tissue samples into the cylindrical openings provided in the recipient block, pouring paraffin onto the recipient block and cooling the recipient block Korean Utility Model Application No. 20-1999-0025914 discloses an apparatus for preparation of a tissue microarray, which comprises a plurality of tissue storing units including a storing cassette to insert a plurality of tissue samples thereinto and to be then filled with paraffin an outer surface thereof; a puncher to punch off the solidified tissue samples at a state of being integrated with the paraffin into a single structure in the storing cassette to provide tissue blocks with a constant diameter; and a block storing unit including a plurality of tissue inserting holes to insert a plurality of the tissue blocks thereinto at a state of being integrated therewith into a single structure.

However, the conventional methods disclosed in the International Patent Application and the Korean Utility Model Application have a significant problem since the above tissue microarrays are prepared using paraffin-embedded tissue blocks. Typically, the paraffin embedding method of tissue samples arrayed in a recipient block includes heating process. During the heating process, paraffin is melted, and this melting of paraffin leads an array of tissue samples to fall into disorder or the tissue samples to be mingled with each other. This problem can be overcome by carrying out the paraffin embedding at low temperatures. However, several hours (5–12 hrs) are required to accomplish paraffin embedding of tissue samples at low temperatures. In this case, tissue samples are often not fused with paraffin, causing separation of the tissue samples from the paraffin block upon sectioning of the resulting tissue microarray. In addition, there is another problem with the conventional parafin-based methods, as follows. Since parafin is opaque white in a solid phase, there is a difficulty in determining states and positions of tissue samples when the tissue samples are arrayed in a recipient block being embedded in paraffin.

DISCLOSURE OF THE INVENTION

According to the present invention, a recipient block is prepared using an additive such as agarose or agar, which is not melted at a heating step during the embedding process and is transparent in a solid phase. As a result tissue samples are not mingled with each other in the resulting tissue microarray due to the agarose or agar's property of being not melted at the heating temperature during the embedding process, and the arrayed state and other states of the tissues are easily evaluated with the naked eye due to the transparency of the agarose or agar in a solid phase.

Therefore, in an aspect, the present invention provides a recipient block for arraying a certain tissue sample into a desired position on a tissue microarray slide, comprising (a) an additive and (b) a wax.

In another aspect, the present invention provides a method of preparing a recipient block, including (1) preparing an aqueous solution of an additive; (2) pouring the aqueous solution of the additive into a mold and cooling the mold to gelate the aqueous solution of the additive; (3) dehydrating the resulting additive gel in alcohol; (4) immersing the dehydrated additive gel in an organic solvent to make the dehydrated additive gel transparent; (5) penetrating a wax into the transparent additive gel to provide a block; and (6) providing a plurality of cylindrical holes in the block.

In a further aspect, the present invention provides a method of preparing a tissue microarray block, including (1) arraying each of certain tissue samples into each of the cylindrical holes of the recipient block as prepared above; and (2) heating the recipient block in which the tissue samples have been arrayed at 50° C. to 70° C. for 20 min to 40 min and cooling the recipient block for embedding of the tissue samples.

BEST MODE FOR CARRYING OUT THE INVENTION

I. Definition of Terms

The term "tissue sample", as used herein, refers to not only all the tissue samples isolated individually from humans, animals and plants but also culture products of microorganisms or cells. The tissue samples may be analyzed by using the recipient block according to the present invention.

Figure 2:
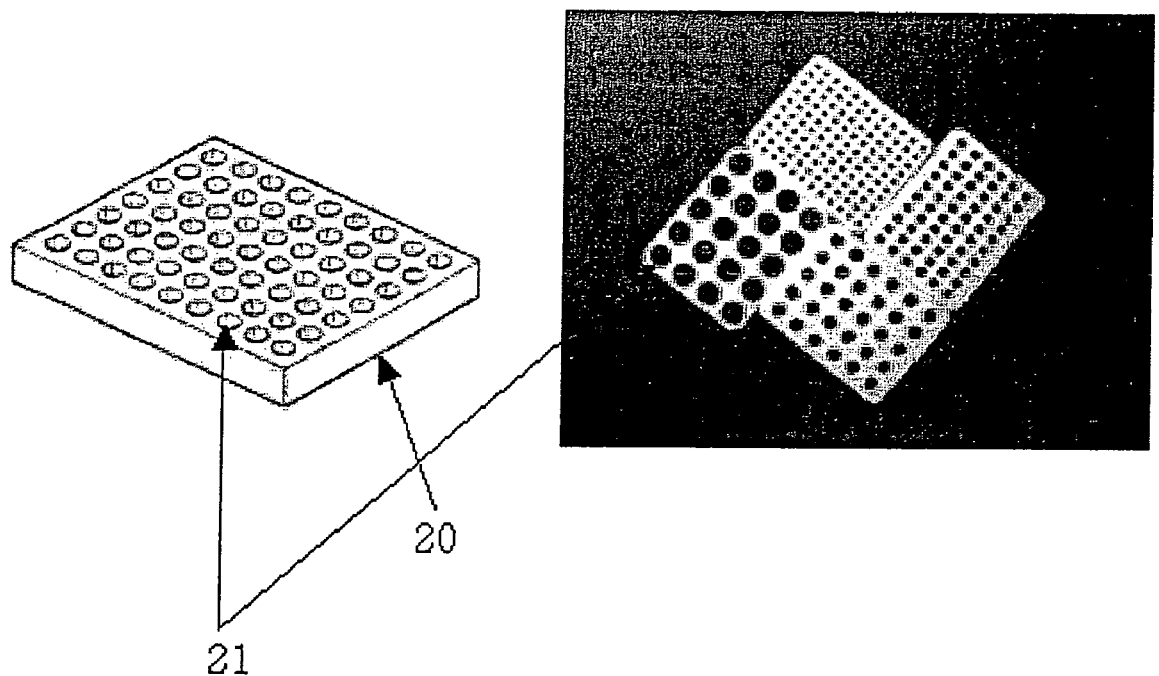
FIG. 2 shows perspective views of a recipient block according to the present invention.
Figure 3:
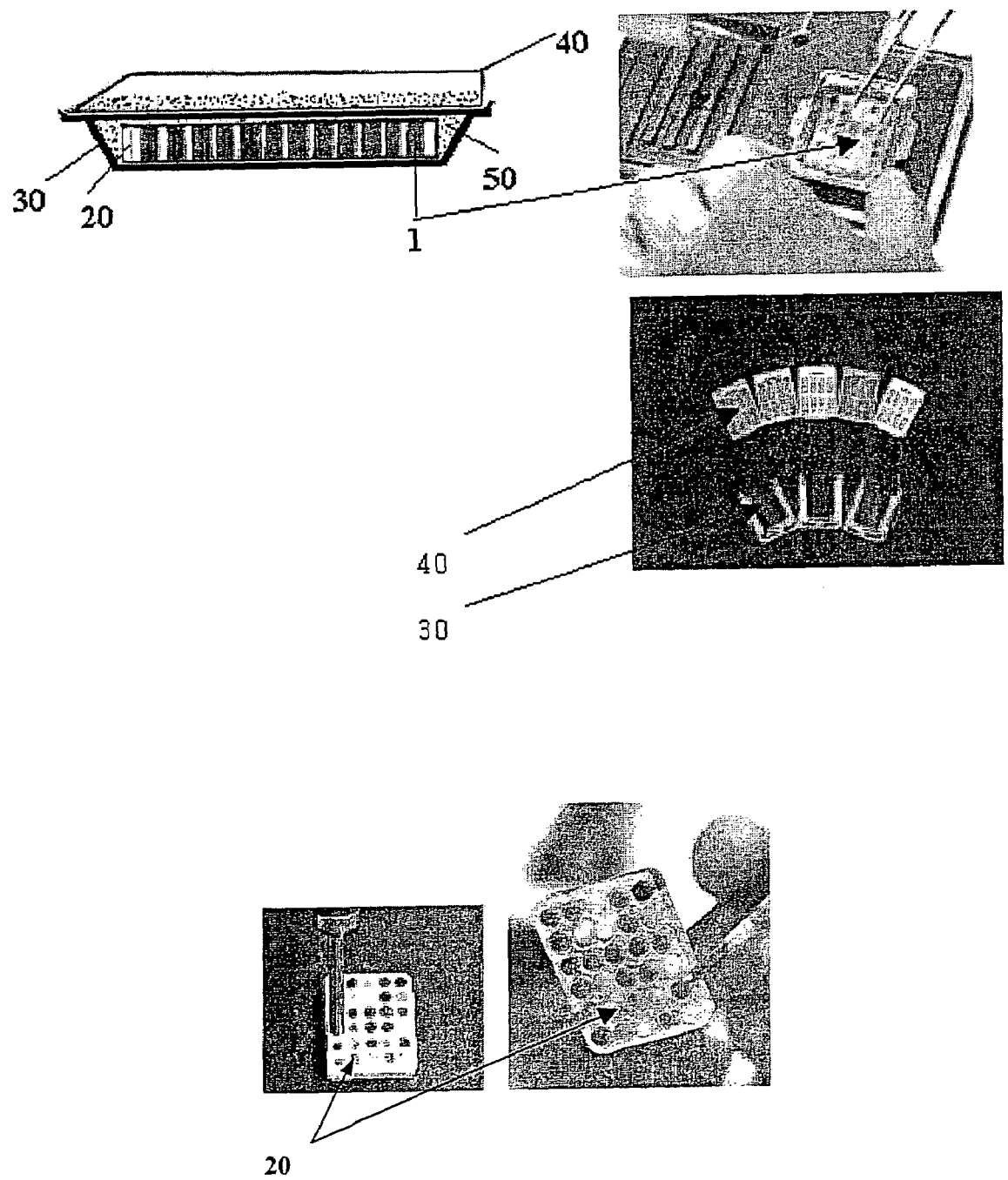
FIG. 3 shows a schematic view of a tissue microarray block prepared by arraying a plurality of tissue samples in the recipient block of the present invention and embedding the tissue samples.
Figure 4:
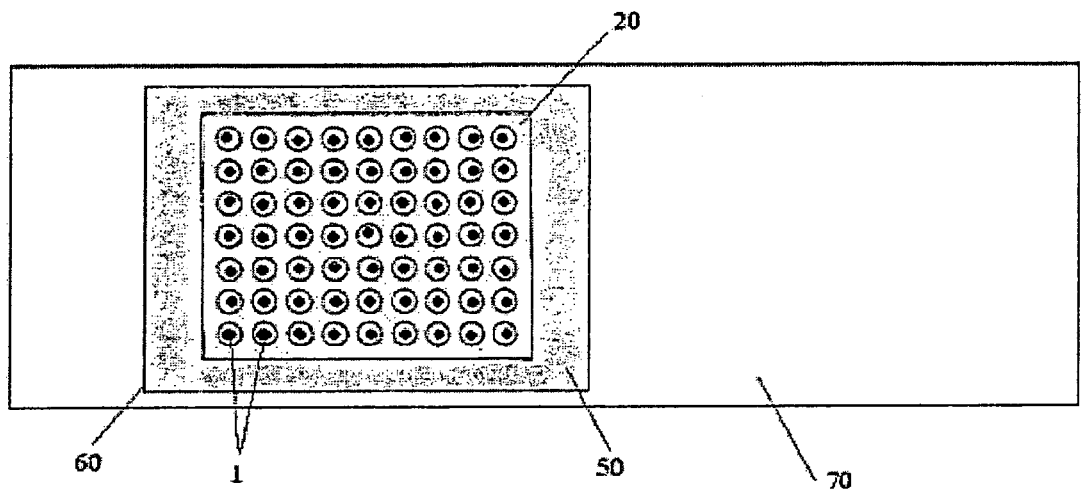
FIG. 4 is a top plane view of a section of the tissue microarray block, which has been attached onto a glass slide.
Figure 4:
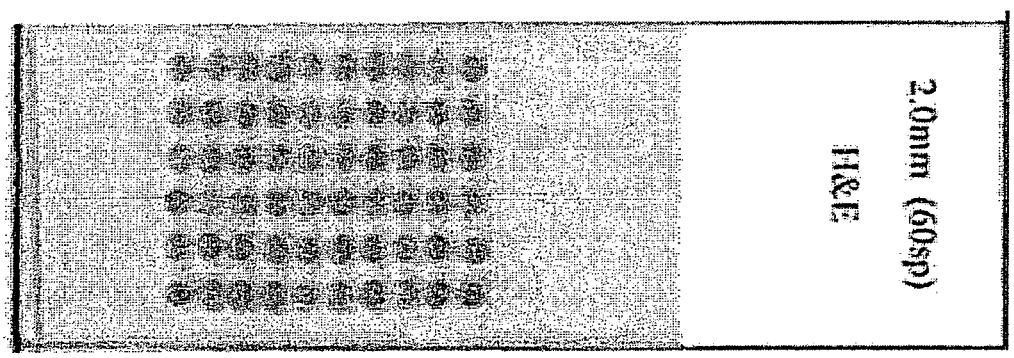
Figure 4:
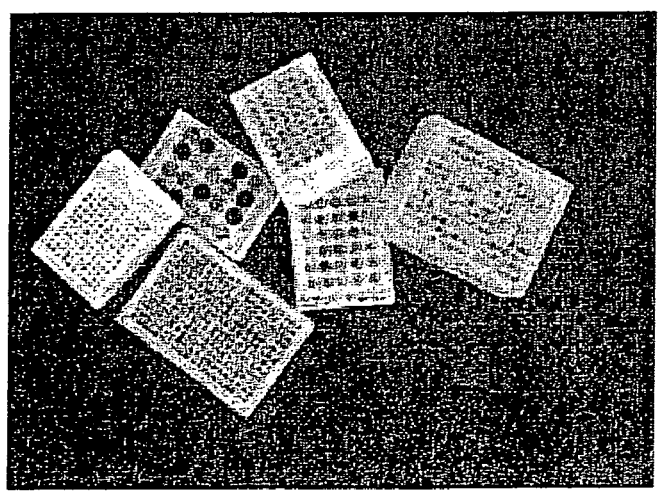

The term "recipient block", as used herein, refers to a unit that serves as a mold to allow each of certain tissue samples to be arrayed in a desired position on a tissue microarray slide (see, FIG. 2). The recipient block includes a plurality of cylindrical holes 21 to receive multiple tissue samples. The cylindrical holes are typically provided in the form of penetrating through the recipient block, but are not limited to the form The term "embedding", as used herein, refers to a process of integrating tissue samples with the recipient block into a single structure by arraying the tissue samples into the cylindrical holes of the recipient block, heating the recipient block to melt the material comprising the recipient block, that is, a small quantity of the wax, and allow the molten wax to penetrate into and surround the tissue samples, and cooling the heated recipient block.

The term "issue microarray block", as used herein, indicates a product obtained by the embedding process, such as arraying tissue samples into the cylindrical holes of the recipient block and heating and cooling the recipient block to fuse the tissue samples with the material comprising the recipient block.

II. Recipient Block and Method of Preparing Thereof

The recipient block according to the present invention is characterized by comprising (a) an additive and (b) a wax.

The term "additive", as used herein, refers to a material that forms a gel at 30° C. to 40° C. and is not melted at lower temperature than 80° C. to 90° C., such as agarose or agar, but is not limited to this material. The additive may be present in a solid phase or a liquid phase. In case of being in a solid phase, the additive may be in the form of powder or gel. Both of the agarose and the agar are gelated at about 35° C. and melted at higher than about 90° C. and has flexibility in a solid phase.

"Waxes" are typically classified into paraffin, microcrystalline waxes, synthetic waxes and natural waxes (e.g., bees wax) according to their source. Even all of them may be used as the material for the recipient block, paraffin microcrystalline waxes and bees wax are preferred and paraffin is preferred the most. "Paraffin" melts at 45° C. to 65° C., and is opaque white in a solid phase. The other waxes have similar physical properties to paraffin.

As noted above, the conventional recipient blocks were prepared by using only paraffin. As apparent from the aforementioned physical properties, paraffin is melted during an embedding process due to its low melting point, leading to mingling of tissue samples. It also has a difficulty in evaluating the array and the states of the tissue samples after being arrayed and embedded due to its opaque white color in a solid phase. Whereas when a recipient block is prepared using only an additive such as agarose or agar, tissue samples arrayed in cylindrical holes of the recipient block cannot be tightly fused into the recipient block, thereby it may cause separation of the tissue samples from the resulting tissue microassay block upon sectioning thereof In this regard, upon preparation of the recipient block according to the present invention, it is important to use (a) the additive and (b) the wax in a proper weight ratio. According to the present invention, the additive is used in an amount of 80% to 99% by weight, preferably 85% to 97.5% by weight, and more preferably 90% to 95% by weight based on the total weight of the recipient block, while the wax is used in an amount of 1% to 20% by weight, preferably 2.5% to 15% by weight, and more preferably 5% to 10% by weight based on the total weight of the recipient block.

The recipient block of the present invention may be prepared by (1) preparing an aqueous solution of an additive; (2) pouring the aqueous solution of the additive into a mold and cooling the mold to gelate the aqueous solution of the additive; (3) dehydrating the resulting additive gel in alcohol; (4) immersing the dehydrated additive gel into an organic solvent to make the dehydrated additive gel transparent; (5) penetrating a wax into the transparent additive gel to provide a block; and (6) providing a plurality of cylindrical holes in the block.

According to the method of preparing a recipient block, the amount of the additive of aqueous solution in step (1) has to be suitable for both offering the additive gel to a proper hardness and supplying enough time for making the surface of the additive gel flat by slow gelation at room temperature. The concentration of the additive in the aqueous solution, suitable for the present invention, is 1% to 10% by weight, preferably 1.5% to 7.5% by weight, and more preferably 2% to 5% by weight.

In step (3), the additive gel obtained in step (2) is hardened by dehydration. In this step, during the additive gel is immersed in alcohol, the alcohol penetrates into the additive gel and the water in the additive gel diffuses to the outside of the additive gel, and the inside of the additive gel is finally filled with the alcohol. In this dehydration step, preferred is to use a lower alkyl alcohol, such as methanol or ethanol, and more preferred is to use ethanol.

On the other hand, if the dehydration is carried out directly in a high concentration of alcohol, the shape of the additive gel may be modified due to high osmotic pressure. For this reason, the dehydration of the additive gel is preferably carried out by starting with a low concentration of alcohol and gradually moving to a high concentration of alcohol. In an aspect of the present invention, the dehydration stats with an about 70% alcohol solution and sequentially moves to alcohol solutions of about 80%, about 90% and about 100%. In addition, when the additive gel is exposed to a high concentration of alcohol for a long period of time, it is excessively hardened, and thus, is easily fractured upon sectioning. For this reason, it is critical to properly set the dehydration time. In an aspect of the present invention the most preferred dehydration is attained when the additive gel is immersed in an about 70% alcohol solution for 1 to 3 hrs, an about 80% alcohol solution for 1 to 3 hrs, an about 90% alcohol solution for 1 to 3 hrs, or an about 100% alcohol (or acetone) solution for 1 to 3 hrs. Thus, the total dehydration time suitable in the present invention ranges from 5 to 10 hrs, preferably 6 to 9 hrs, and more preferably 7 to 8 hrs.

In step (4) the alcohol penetrated into the additive gel in the previous step is removed from the dehydrated additive gel. It is typically called a "clearing step". The removal of alcohol may be attained by immersing the dehydrated additive gel in an organic solvent which will be specified, as follows. The examples of the organic solvent useful in the clearing step include xylene, toluene, chloroform and benzene which are not limited to thereof. Xylene is mostly preferable. On the other hand, the time required for the clearing step is 3 to 8 hrs, preferably 4 to 7 hrs, and more preferably 5 to 6 hrs.

In step (5), a proper solidity is provided to the additive gel obtained in the previous step to prevent its modification. During the additive gel is immersed in a liquefied wax, the wax penetrates into the additive gel. While the additive gel is cooled, it allows to harden the penetrated wax, and provides a hard block. The wax suitable for the present invention is preferably paraffin, a microcrystaline wax or bees wax.

On the other hand, when the penetration of the wax into the additive gel is performed for a very short period, the organic solvent remains in the additive gel while the sufficient penetration of the wax into the additive gel is not attained, leading to an incomplete hardening of the additive gel. The additive gel, which is not completely hardened, is difficult to be cut into a constant thickness (48 µm) upon sectioning. In contrast, a very long penetration time causes the shrinkage or extreme hardening of the additive gel and such an additive gel is easily fractured upon sectioning. Thus, it is important to properly set the penetration time of the wax. The penetration time of the wax suitable for the present invention ranges from 2 to 7 hrs, preferably 3 to 6 hrs, and more preferably 4 to 5 hrs.

A desired recipient block may be prepared by forming a plurality of cylindrical holes with a constant diameter (e.g., 1 mm, 2 mm, 3 mm, 5 mm, etc.) in the block obtained through steps (1) to (5). Each of the cylindrical holes may be formed by using a manual tool capable of forming holes, such as a gimlet, or using a puncher. In case of using a puncher, the puncher preferably has the same size of inner diameter hole of a punching tip of a tissue puncher typically used in tissue isolation.

In addition, the recipient block of the present invention may be prepared using a pre-gelated additive as a starting material. In this case, from the above method of preparing a recipient block, steps (1) and (2) are omitted, and step (3) is carried out as a fist step. If desired, before step (3) is carried out, a step of cutting the pre-gelated additive into a desired size and a desired form may precede.

III. Method of Preparing a Tissue Microarray Block

In a further aspect, the present invention provides a method of preparing a tissue microarray block, including (1) arraying each of certain tissue samples into each of the cylindrical holes of the recipient block according to the present invention; and (2) heating the recipient block in which the tissue samples have been arrayed at 50° C. to 70° C. for 20 min to 40 min and cooling the recipient block for embedding of the tissue samples.

In the method of preparing the tissue microarray block, since the recipient block according to the present invention is not melted at a high temperature by containing the additive with a distinct melting point from the wax, embedding of the arrayed tissue samples is attained by heating the recipient block at about 60° C., higher than upon the conventional embedding, for a short time (about 30 min).

In the method of preparing a tissue microarray block, a solid tissue microarray block may be produced by pouring a small quantity of a wax onto the recipient block after the heating in step (2) and cooling the recipient block. In this case, after the step of pouring the wax onto the recipient block, the recipient block is preferably covered with a cassette. This is because the tissue microarray block is, upon sectioning, easily attached onto and detached from a tissue microtome having a holder fitting into the cassette, which is generally used for the sectioning of a final tissue microarray block.

EXAMPLES

1. Preparation of a Recipient Block 100 ml of distilled water and 4 g of agarose were added to a beaker, and the beaker was heated to melt the agarose. The molten agarose was poured into a mold, and slowly cooled to room temperature for its gelation. After being detached from the mold, the agarose gel was dehydrated by being immersed in a 70% alcohol solution for 2 hrs, an 80% alcohol solution for 2 hrs, a 90% alcohol solution for 2 hrs, and then a 100% alcohol solution for 2 hrs. The dehydrated agarose gel was immersed in xylene for 6 hrs to make the gel clear, and penetrated with paraffin for 5 hrs, to provide a block.

Figure 1:
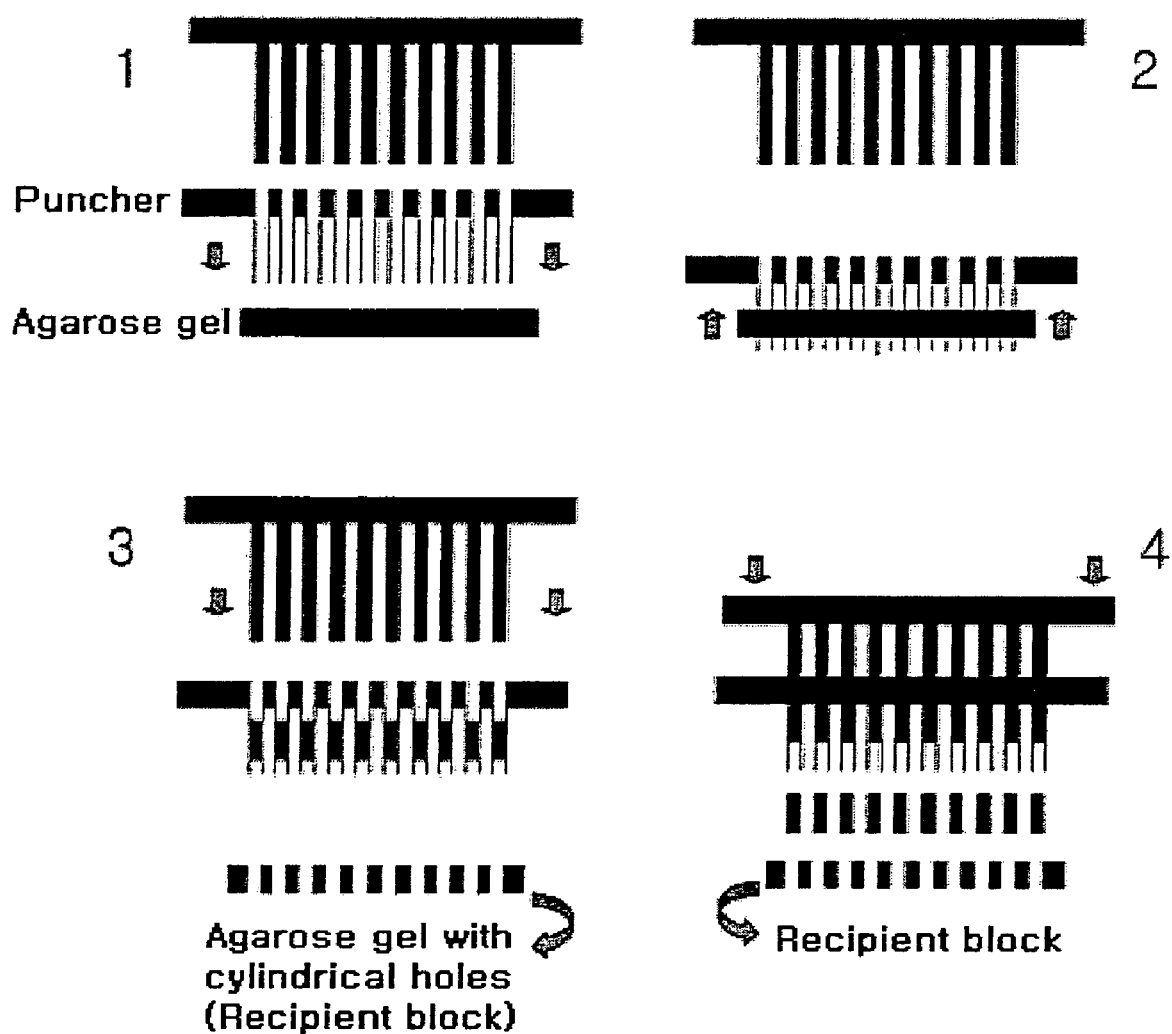
FIG. 1 shows a schematic view of a process of providing cylindrical holes to the block according to the present invention using a puncher.

The resulting block was cut into a size suitable for its fitting into the inner space of a base mold 30. Then, the block was punched with a puncher having punching needles with the same inner diameter as a through hole of a punching tip of a tissue puncher. The puncher was removed from the block to completely form cylindrical holes in the block. Agarose gel inserted into the inner space of the punching needles was removed using a roller (see, FIG. 1).

2. Preparation of a Tissue Microarray Block

The recipient block 20 into which tissue samples had been arrayed was placed into an iron base mold 30 in a direction of downward placing a surface to be cut thereof, and incubated in an oven at 60° C. for 30 min. After the incubation, the recipient block 20 in the base mold 30 was turned to a transparent solid that was visually transparent to the arrayed tissue samples. After the transparent recipient block was taken out from the base mold, it was added with a small quantity of paraffin and covered with a cassette 40, followed by incubation on a cold plate for solidification of the added paraffin After complete solidification, the cassette was separated from the base mold 30 to give a tissue microarray block.

Then, the tissue microarray block was cut into a thin size (4–8 µm) using a tissue microtome. Each of the sections 60 was attached onto a glass slide 70, and subjected to a desired histochemical study, and microscopically evaluated.

INDUSTRIAL APPLICABILITY

As described above, the recipient block according to the present invention facilitates arraying and fixing of each of certain tissue samples into a desired position on a slide, thereby allowing for rapid and faithful preparation of a tissue microarray block for multiple tissue samples and securing rapid and accurate evaluation of the multiple tissue samples. Therefore, the recipient block and the method of preparing a tissue microarray using the recipient block according to the present invention are very useful in the bioengineering and medical fields.

What is claimed is:

1. A recipient block for arraying a certain tissue sample into a desired position on a tissue microarray slide, comprising (a) agarose or agar in an amount of 80% to 99% by weight based on a total weight of the recipient block and (b) wax in an amount of 1% to 20% by weight based on a total weight of the recipient block, wherein the said recipient block comprises of a plurality of cylindrical holes to receive multiple tissue samples.

2. The recipient block as set forth in claim 1, wherein the wax is paraffin, a microcrystalline wax, or bees wax.

3. A method of preparing a recipient block of claim 1, comprising the steps of:
   (1) preparing an aqueous solution of an agarose or agar;
   (2) pouring the aqueous solution of the agarose or agar into a mold and cooling the mold to gelate the aqueous solution of the agarose or agar;
   (3) dehydrating the resulting agarose or agar gel in alcohol;
   (4) immersing the dehydrated agarose or agar gel in an organic solvent to make the dehydrated agarose or agar gel transparent;
   (5) penetrating a wax into the transparent agarose or agar gel to provide a block; and
   (6) providing a plurality of cylindrical holes in the block.

4. The method as set forth in claim 3, wherein the agarose or agar is contained in the recipient block in an amount of 80% to 99% by weight based on a total weight of the recipient block.

5. The method as set forth in claim 3, wherein the wax is contained in the recipient block in an amount of 1% to 20% by weight based on a total weight of the recipient block.

6. The method as set forth in claim 3, wherein the wax is paraffin, a microcrystalline wax or bees wax.

7. The method as set forth in claim 3, wherein the said aqueous solution of step (1) contains agarose or agar in an amount of 1% to 10% by weight.

8. The method as set forth in claim 3, wherein the dehydration of step (3) is attained by immersing the agarose or agar gel in an about 70% alcohol solution for 1 to 3 hrs, an about 80% alcohol solution for 1 to 3 hrs, an about 90% alcohol solution for 1 to 3 hrs, or an about 100% alcohol or acetone solution for 1 to 3 hrs.

9. The method as set forth in claim 3, wherein the clearing of step (4) is attained by immersing the agarose or agar gel into the organic solvent for 3 to 8 hrs.

10. The method as set forth in claim 3, wherein the penetration of step (5) is carried out for 2 to 7 hours.

11. The method as set forth in claim 3, wherein, when the agarose or agar is in a gel form, both of the steps (1) and (2) are omitted and step (3) is carried out as a first step.

12. A method of preparing a tissue microarray block, comprising the steps of:
   (1) arraying each of certain tissue samples into each of the cylindrical holes of the recipient block of claim 1; and
   (2) heating the recipient block in which the tissue samples have been arrayed to 50° C. to 70° C. for 20 min to 40 min and cooling the recipient block for embedding of the tissue samples.

13. The method as set forth in claim 12, wherein, in step (2), the recipient block in which the tissue samples have been arrayed is heated at about 60° C. for amount 30 min and cooled for embedding of the tissue samples.

14. The method as set forth in claim 12, wherein a small quantity of paraffin is poured onto the recipient block before the cooling in step (2).

15. The method as set forth in claim 13, wherein a small quantity of paraffin is poured onto the recipient block before the cooling in step (2).

16. The method as set forth in claim 5, wherein the wax is paraffin, a microcrystalline wax or bees wax.

17. The method as set forth in claim 12, wherein the percentage of the agarose or agar (a) is contained in the recipient block in an amount of 80% to 99% by weight based on a total weight of the recipient block.

18. The method as set forth in claim 12, wherein the wax (b) is contained in the recipient block in an amount of 1% to 20% by weight based on a total weight of the recipient block.

19. The method as set forth in claim 12, wherein the wax is paraffin, a microcrystalline wax or bees wax.

* * * * *